United States Patent
Wu et al.

(10) Patent No.: US 6,388,079 B1
(45) Date of Patent: May 14, 2002

(54) PROCESS FOR PREPARING PERGOLIDE

(75) Inventors: Edwin S. C. Wu, Tainan; Mark Wu, Taipei Hsien, both of (TW)

(73) Assignee: Scinopharm Singapore Pte Ltd., Singapore (SG)

( * ) Notice: Subject to any disclaimer, the term of this patent is extended or adjusted under 35 U.S.C. 154(b) by 23 days.

(21) Appl. No.: 09/651,381

(22) Filed: Aug. 29, 2000

(51) Int. Cl.$^7$ ................ C07D 471/04; C07D 457/02
(52) U.S. Cl. ............................... 546/67; 546/68
(58) Field of Search .................... 546/67, 68

(56) References Cited

U.S. PATENT DOCUMENTS

| | | | |
|---|---|---|---|
| 4,166,182 A | | 8/1979 | Kornfeld et al. ............... 546/67 |
| 4,180,582 A | * | 12/1979 | Kornfeld et al. ............. 514/285 |
| 4,202,979 A | * | 5/1980 | Kornfeld et al. ............... 546/67 |
| 4,246,265 A | * | 1/1981 | Kornfeld et al. ............. 514/285 |
| 5,219,862 A | * | 6/1993 | Sauer et al. ................. 514/288 |
| 5,463,060 A | | 10/1995 | Misner ........................ 546/68 |

* cited by examiner

*Primary Examiner*—Alan L. Rotman
(74) *Attorney, Agent, or Firm*—Jenkens & Gilchrist, P.C.

(57) ABSTRACT

This invention relates to a process for preparing pergolide, which comprises the steps of reacting 9,10-dihydrolysergol with an acid anhydride at an elevated temperature in the presence of a catalyst to form a triacylated product intermediate; reducing the triacylated product intermediate with a reducing agent in a solvent to form a primary amino alcohol intermediate; and reacting the amino alcohol intermediate with dimethyl disulfide and trialkyl phosphine, aryl phosphine or the polymeric derivatives of phosphine analogs thereof in a polar solvent to obtain pergolide; or the steps of reacting 9,10-dihydrolysergol with dimethyl disulfide and trialkyl phosphine, aryl phosphine or the polymeric derivatives of phosphine analogs thereof in a polar solvent to form a methylsulfide intermediate; reacting the methylsulfide intermediate with an acid anhydride at an elevated temperature in the presence of a catalyst to form a diacylated amide intermediate; and reducing the diacylated amide intermediate with a reducing agent in a solvent to obtain pergolide.

21 Claims, No Drawings

PROCESS FOR PREPARING PERGOLIDE

FIELD OF THE INVENTION

This invention relates to a process for the preparation of pergolide, which utilizes 9,10-dihydrolysergol as a starting material. This process is a three-step synthesis procedure which involves acylation-dealkylation, reduction and sulfide formation. Pergolide can be obtained from 9,10-dihydrolysergol by either conducting acylation-dealkylation before sulfide formation in the procedure or vise versa.

BACKGROUND OF THE INVENTION

Pergolide is a well-known drug particularly useful for the treatment of Parkinson's disease. U.S. Pat. No. 4,166,182, issued to Kornfeld and Bach on Aug. 28, 1979, assigned to Eli Lilly and Company, first discloses pergolide and its derivatives, their pharmaceutical use, and a 7-step synthesis of pergolide starting from 9,10-dihydrolysergic acid. The 7-step process is shown in Scheme I:

Scheme I

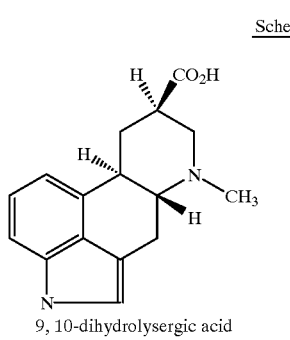
9, 10-dihydrolysergic acid

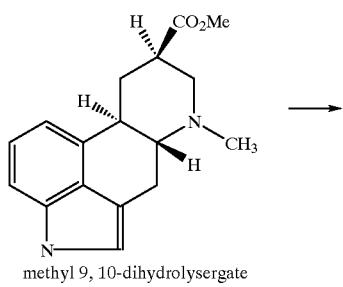
methyl 9, 10-dihydrolysergate

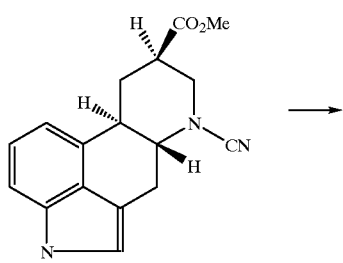

-continued

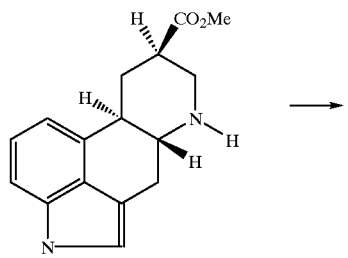

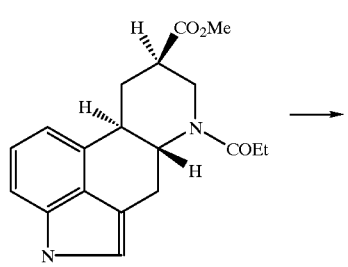

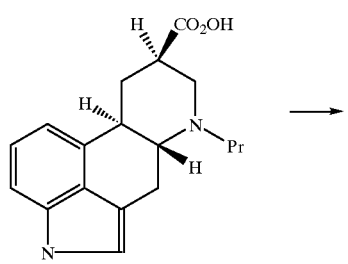

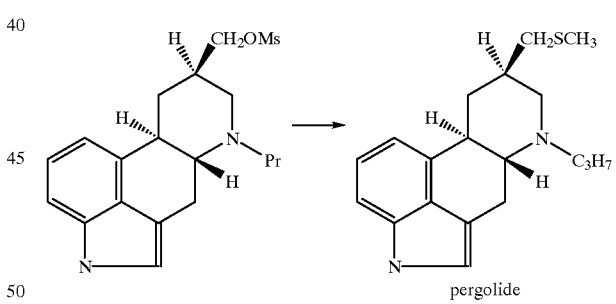
pergolide

Since this process is too complex and not economically effective, improvements for the synthesis of pergolide have been studied and developed. U.S. Pat. No. 5,463,060, issued on Oct. 31, 1995 to Misner, assigned to Eli Lilly and Company, discloses a one-pot process for preparing pergolide from 9,10-dihydrolysergol (8,9-dihydroelymoclavine, as referred to in U.S. Pat. No. 5,463,060). The starting material, 9,10-dihydrolysergol, reacts first with 1-iodopropane, followed by sulfonyl halide, and an alkali metal thiomethoxide to give pergolide without isolating intermediate products, as shown in Scheme II:

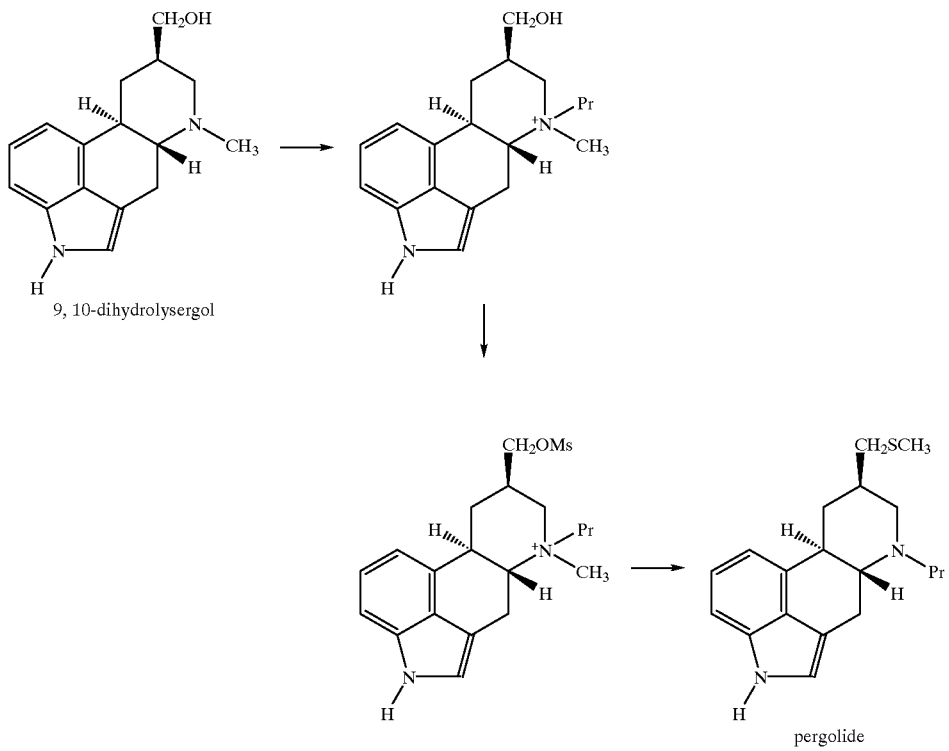

Scheme II 9, 10-dihydrolysergol pergolide

The present invention provides a novel process for the preparation of pergolide from 9,10-dihydrolysergol through different routes. This new process is directed to a quick and economical synthesis procedure that involves three steps.

SUMMARY OF THE INVENTION

This invention relates to a process for preparing pergolide from 9,10-dihydrolysergol via an acylamide intermediate with two alternative routes. The process comprises reacting 9,10-dihydrolysergol with an acid anhydride at an elevated temperature in the presence of a catalyst to form a triacylated product intermediate; reducing the triacylated product intermediate with a reducing agent in a solvent to form a primary amino alcohol intermediate; and reacting the amino alcohol intermediate with dimethyl disulfide and trialkyl phosphine, aryl phosphine or the polymeric derivatives of phosphine analogs thereof in a polar solvent to obtain pergolide.

The alternative process comprises reacting 9,10-dihydrolysergol with dimethyl disulfide and trialkyl phosphine, aryl phosphine or the polymeric derivatives of phosphine analogs thereof in a polar solvent to form a methylsulfide intermediate; reacting the methylsulfide intermediate with an acid anhydride at an elevated temperature in the presence of a catalyst to form a diacylated amide intermediate; and reducing the diacylated amide intermediate with a reducing agent in a solvent to obtain pergolide.

DETAILED DESCRIPTION OF THE INVENTION

As used herein, Me is methyl; Et is ethyl; Pr is propyl; Bu is butyl; and Ms is mesyl.

The process for preparing pergolide of the invention comprises the following steps:

(a) reacting 9,10-dihydrolysergol (1) with an acid anhydride at an elevated temperature in the presence of a catalyst to form the corresponding triacylated product (5);

(b) reducing the triacylated product (5) with a reducing agent in a solvent to form the corresponding primary amino alcohol (6); and (c) reacting the amino alcohol (6) with dimethyl disulfide and a trialkyl phosphine, aryl phosphine or the polymeric derivatives of phosphine analogs thereof, in a polar solvent to form the pergolide product (4).

The reaction procedure is shown in scheme III:

Scheme III

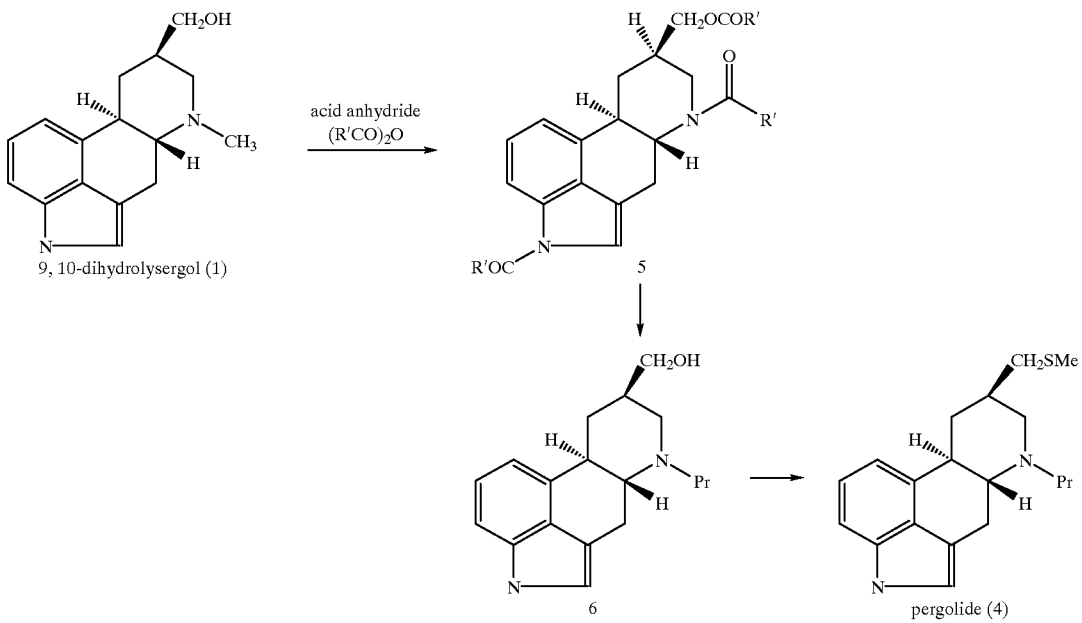

Step (a) of this process refers to acylation-dealkylation. Gerszberg et al. reported (S. Gerszberg et al. *Tet. Lett.* 1973 (15), 1269–1272) that acylation-dealkylation of a few simple tertiary amines to the corresponding amides in the presence of an acid anhydride was met with varying degree of success (18–62% yield).

The starting material, 9,10-dihydrolysergol, can be prepared according to the process disclosed in the aforementioned U.S. Pat. No. 4,166,182 or any method known in the state of the art.

For step (a) of this process, the suitable acid anhydride has the formula of $(R'CO)_2O$ wherein R' is $C_1-C_4$ alkyl, i.e. the acid anhydride can be selected from the group consisting of acetic anhydride, propionic anhydride, butyric anhydride, and pentanoic anhydride. For acylation-dealkylation, the excess of the acid anhydride is used to ensure the completion of tri-acylation of 9,10-dihydrolysergol to the corresponding triacylated product.

The acylation-dealkylation is conducted at an elevated temperature, preferably at the refluxing temperature of the reaction mixture, more preferably in the range of 100° C. to 200° C., normally for 24–60 hours. The catalyst for acylation-dealkylation is preferably selected from sodium iodide (NaI) and dimethylaminopyridine (DMAP), more preferably NaI.

The acylation-dealkylation can be optionally conducted in the presence of a solvent for the modification of the reaction, but preferably without a solvent. The solvents suitable for the reaction can be highly polar solvents, such as those disclosed in the afore-mentioned U.S. Pat. No. 5,463,060, preferably 1-methyl-2-pyrolidinone and the related six-ring compounds thereof.

Step (b) of this process refers to a reduction reaction. The suitable reducing agent is a metal hydride, preferably lithium aluminum hydride (LAH) and Vitride®, more preferably LAH. The reaction temperature is not critical. Normally, the reduction is conducted at a temperature in the range of −30° C. to the refluxing temperature of the reaction mixture, preferably in the range of 0° C. to 80° C., more preferably in the range of 0° C. to room temperature. The reduction is conducted in the presence of an ethereal solvent, preferably tetrahydrofuran (THF).

Step (c) of this process refers to sulfide formation. An excess of dimethyl disulfide and a large excess of trialkyl phosphine, aryl phosphine or the polymeric derivatives of phosphine analogs thereof are normally used to achieve the formation of a methyl sulfide intermediate. In sulfide formation, the trialkyl phosphine used has the formula of $R_3P$, wherein R is $(CH_2)_n$ and n is 1–6. The aryl phosphine used has the formula of $Ar_3P$, wherein Ar is phenyl or substituted phenyl. The reaction temperature is not critical. Normally, the sulfide formation can be conducted at a temperature in the range of 0° C. to 150° C. The polar solvents suitable for the sulfide formation are preferably dimethyl formamide (DMF) and dimethylsulfoxide (DMSO), more preferably DMF.

One of the preferred embodiments of this process comprises the following steps:

(a) reacting 9,10-dihydrolysergol (1) with propionic anhydride and sodium iodide at a temperature of about 160° C. to form the corresponding propionamide (5a);

(b) reducing the propionamide (5a) by lithium aluminum hydride (LAH) in tetrahydrofuran (THF) at room temperature to form the corresponding primary amino alcohol (6a); and (c) reacting the amino alcohol (6a) with an excess of dimethyldisulfide ($Me_2S_2$) and a large excess of tributylphosphine ($Bu_3P$) in dimethyl formamide at a temperature of about 90° C. to obtain the pergolide product (4).

The reaction procedure is shown in scheme IV:

Scheme IV

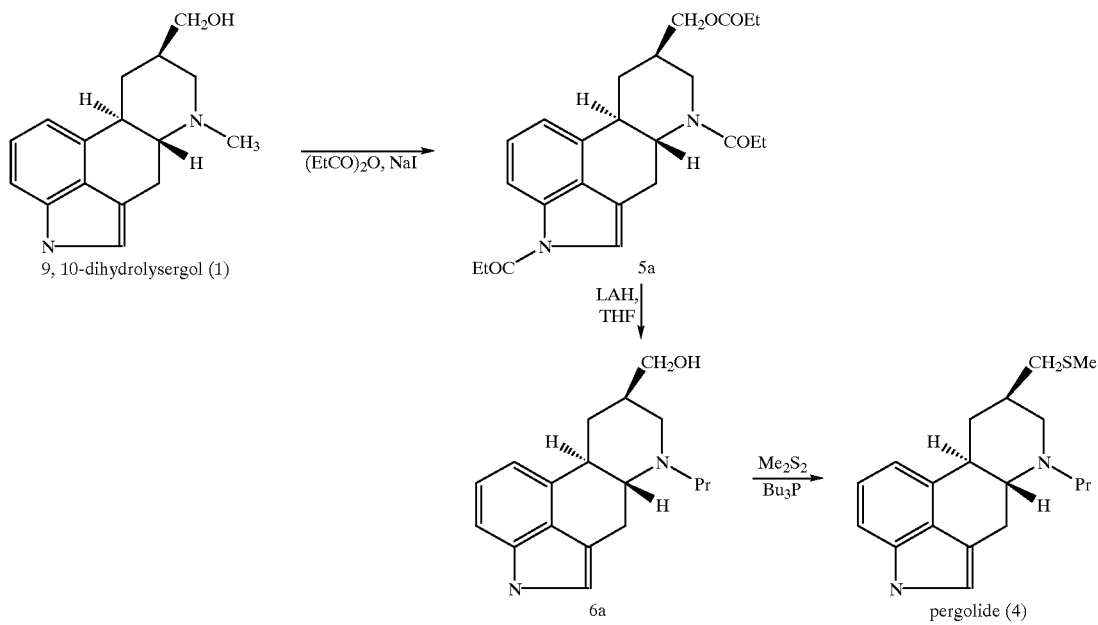

The alternative process for preparing pergolide of the invention comprises the following steps:
(a) reacting 9,10-dihydrolysergol (1) with dimethyl disulfide and a trialkyl phosphine, aryl phosphine or the polymeric derivatives of phosphine analogs thereof, in a polar solvent to form the corresponding methyl sulfide (7);
(b) reacting the methyl sulfide (7) with an acid anhydride at an elevated temperature in the presence of a catalyst to form the corresponding diacylated amide intermediate (8); and
(c) reducing the diacylated amide (8) with a reducing agent in a solvent to obtain the pergolide product (4).

The reaction procedure is shown in scheme V:

Scheme V

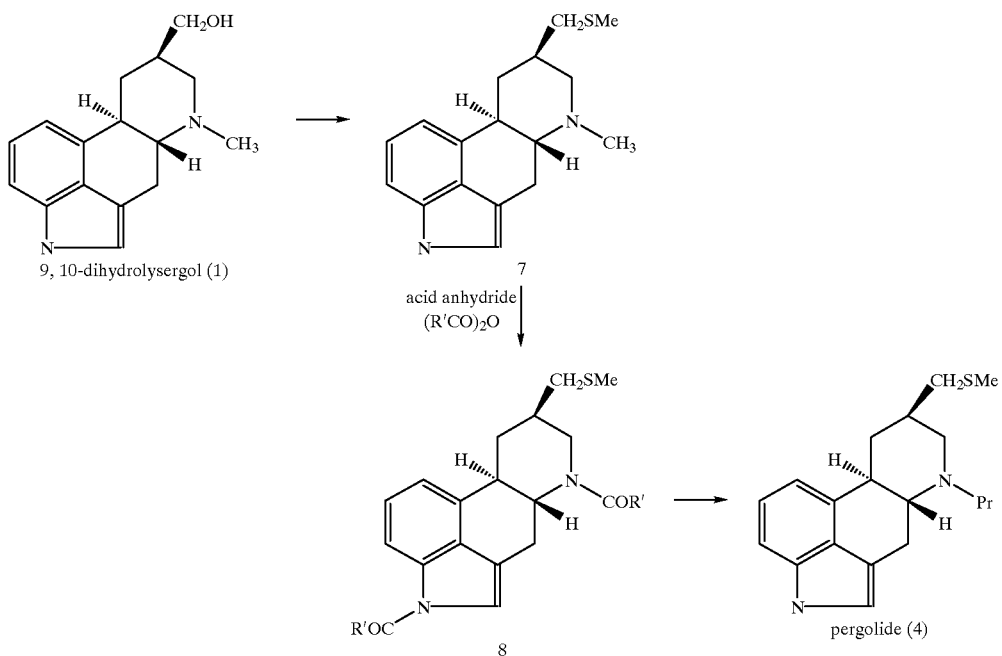

Step (a) of this process refers to sulfide formation. The starting material, 9,10-dihydrolysergol, can be prepared according to the process disclosed in the aforementioned U.S. Pat. No. 4,166,182 or any method known in the state of the art. An excess of dimethyl disulfide and a large excess of trialkyl phosphine, aryl phosphine or the polymeric derivatives of phosphine analogs thereof are normally used to ensure the completion of sulfide formation. The trialkyl phosphine has the formula of $R_3P$, wherein R is $(CH_2)_n$ and n is 1–6. The aryl phosphine has the formula of $Ar_3P$ wherein Ar is phenyl or substituted phenyl. The reaction temperature is not critical. Normally, the sulfide formation can be conducted at a temperature in the range of 0° C. to 150° C. The polar solvents suitable for the sulfide formation are preferably dimethyl formamide (DMF) and dimethylsulfoxide (DMSO), more preferably DMF.

Step (b) of this process refers to acylation-dealkylation. Gerszberg et al. reported (S. Gerszberg et al. *Tet. Lett.* 1973 (15), 1269–1272) that acylation-dealkylation of a few simple tertiary amines to the corresponding amides in the presence of acid anhydride was met with varying degree of success (18–62% yield).

In step (b) of this process, the acid anhydride used has the formula of $(R'CO)_2O$, wherein R' is $C_1$–$C_4$ alkyl, i.e. the acid anhydride can be selected from the group consisting of acetic anhydride, propionic anhydride, butyric anhydride, and pentanoic anhydride. For acylation-dealkylation, an excess of the acid anhydride is used to ensure the completion of di-acylation to form a di-acylamide intermediate.

The acylation-dealkylation is conducted at an elevated temperature, preferably at the refluxing temperature of the reaction mixture, more preferably in the range of 100° C. to 200° C., normally for 24–60 hours. The catalyst used is preferably selected from sodium iodide (NaI) and dimethylaminopyridine (DMAP), more preferably NaI.

The acylation-dealkylation can be optionally conducted in the presence of a solvent for modification of the reaction, but preferably without a solvent. The solvents suitable for the reaction can be highly polar solvents, such as those as disclosed in the afore-mentioned U.S. Pat. No. 5,463,060, preferably 1-methyl-2-pyrolidinone and the related six-ring compounds thereof Step (c) of this process refers to a reduction reaction. The suitable reducing agent is a metal hydride, preferably lithium aluminum, hydride (LAH) and Vitride®, more preferably LAH. The reaction temperature is not critical. Normally, the reduction is conducted at a temperature in the range of –30° C. to the refluxing temperature of the reaction mixture, preferably in the range of 0° C. to 80° C., more preferably in the range of 0° C. to room temperature. The reduction is conducted in the presence of an etheral solvent, preferably tetrahydrofuran (THF).

One of the preferred embodiments of this alternative process comprises the following steps:

(a) reacting 9,10-dihydrolysergol (1) with an excess of dimethyl disulfide ($Me_2S_2$) and a large excess of tributylphosphine ($Bu_3P$) in dimethyl formamide at a temperature of about 90° C. to form the corresponding methylsulfide (7a);

(b) reacting the methylsulfide (7a) with propionic anhydride in the presence of sodium iodide at a temperature of about 160° C. to form the corresponding di-propionamide (8a); and (c) reducing the di-propionamide (8a) with lithium aluminum hydride (LAH) in tetrahydrofuran (THF) at room temperature to obtain the pergolide product (4).

The reaction procedure is shown in scheme VI:

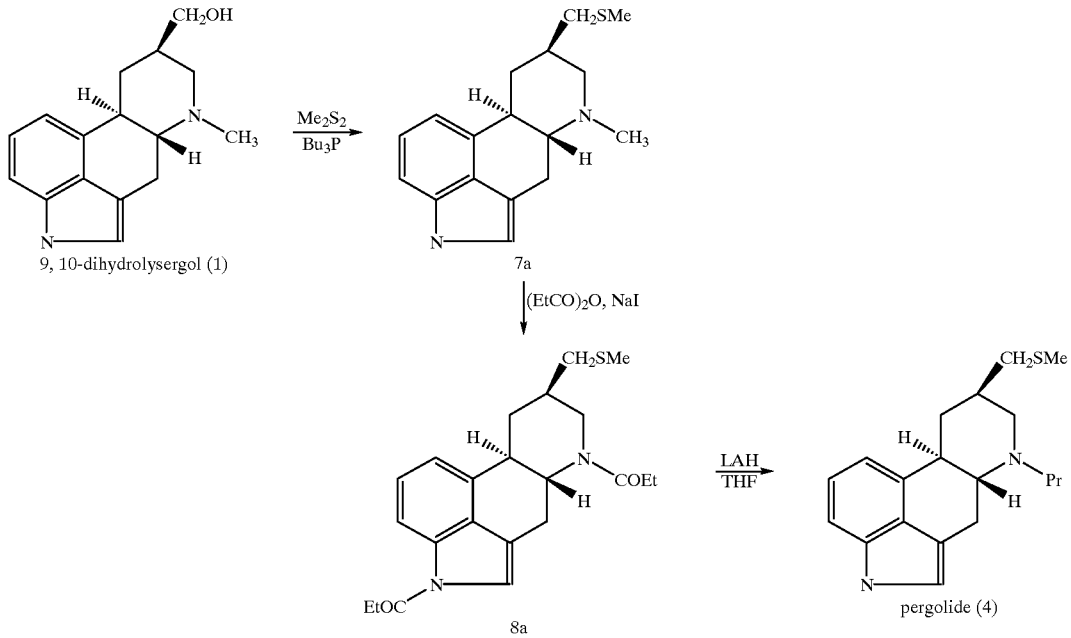

Scheme VI

In order to facilitate a greater understanding of the invention, the following examples are set forth for illustration purposes only and are not to be construed as limits on the present invention.

WORKING EXAMPLES

Example 1

Preparation of D-1,6-dipropionyl-8β-(propionyloxymethyl)ergoline (5a)

A solution of 9,10-dihydrolysergol (1) (2.16 g, 0.0084 mole) and NaI (7.64 g, 0.0506 mol) in the 50 mL of propionic anhydride was refluxed for 48 hours (S. Gerszberg et al., *Tet. Lett.* 1973 (15), 1269–1272). The reaction mixture was quenched with a 10% $Na_2CO_3$ solution and extracted by ethyl acetate. The combined organic layers were dried with brine, magnesium sulfate and concentrated to give an oily residue. The residue was purified by a column chromatograph (silica gel) eluting with 66% ethyl acetate/n-hexane to give 2.06 g of a solid 5a (yield: 60%).

Example 2

Preparation of D-1,6-dibutyroyl-8β-(butyroyloxymethyl)ergoline (5b)

Similarly to the preparation of Example 1, a mixture of 9,10-dihydrolysergol (1) (0.51 g, 0.00195 mol) with butyric anhydride (18 mL) and sodium iodide (1.08 g, 0.00719 mol) was heated at 200° C. to give, after column purification, a solid, 0.583 g (66% yield), mp 151–152° C., elemental analysis:

Cacld: C, 71.09; H, 8.02; N, 6.19; Found: C, 71.52; H, 7.97; N, 5.92.

Example 3

Preparation of D-6n-propyl-8β-hydroxymethylergoline (6a)

LAH (0.91 mg, 0.024 mol) was slowly added to a solution of 5a (1.30 g, 0.0032 mol) in the 130 mL anhydrous THF at 0 ° C. under a nitrogen atmosphere. The reaction mixture was stirred at 0° C. for 30 min and then at room temperature for 4 hours. The reaction was cooled to 0° C. and 0.9 mL of water was slowly added and stirred at 0° C. for 10 min. 2.7 mL of 15% NaOH (aq) and 2.7 mL of water were added dropwise and sequentially. The mixture was stirred for 30 min. at room temperature and was then filtered. Evaporation of the filtrate under vacuum gave 0.71 g of oil 6a (yield: 78%).

Example 4

Preparation of D-6-methyl-8β-(methylthiomethyl)ergoline (7a)

Dimethyl disulfide (73.6 mL, 0.79 mol) and tri-n-butylphosphine (79.6 mL, 0.32 mol) were added to a solution of 1 (8.1 g, 0.032 mol) in the 150 mL of anhydrous DMF and were stirred at room temperature for 6 hours under a nitrogen atmosphere. Dimethyl disulfide of the reaction mixture was removed under reduced pressure to give a residue. A solution of the residue in ethyl acetate was extracted with 3.7% HCl(aq). The aqueous layer was basified with ammonium hydroxide to a pH of 10 and then extracted with ethyl acetate. Removal of ethyl acetate followed by a silica gel column purification eluting with 10% $MeOH/CH_2Cl_2$ gave 5.5 g (yield: 60%) of the title compound 7a.

Example 5

Preparation of D-1,6-dipropionyl-8β(methylthiomethyl)ergoline (8a)

A solution of 7a (0.4 g, 0.0014 mol) and NaI (0.63 g, 0.0042 mol) in 10 mL of propionic anhydride was refluxed for 40 hours. The reaction mixture was quenched with a 10% $Na_2CO_3$ solution and extracted by ethyl acetate (2x). The combined organic layers were washed with a saturated brine solution, dried with magnesium sulfate and concentrated to produce oil. The oil was purified by a silica gel column, eluting with 10% $MeOH/CH_2Cl_{12}$ to give 0.33 g of solid 8a, yield: 60%.

Example 6

Preparation of Pergolide (4) from 6a

Dimethyl disulfide (5.4 mL, 0.0575 mol) and tri-n-butylphosphine (5.71 mL, 0.023 mol) were added to a solution of 6a (0.65 g, 0.0023 mol) in the 20 mL of anhydrous DMF and were stirred at room temperature for 15 hours under a nitrogen atmosphere (R. S. Glass, et al. *J. Org. Chem.* 1982, 47, 2761–2764). Dimethyl disulfide of the reaction mixture was removed under reduced pressure to give a residue. The residue was dissolved in ethyl acetate and extracted with 3.7% aq HCl. The acidic solution was treated with an ammonia solution until pH was 10. The water layer was extracted with ethyl acetate and the ethyl acetate was removed to produce a residue. The residue was then purified by a silica gel column eluting with 50% ethyl acetate/n-hexane to give the title compound as a solid 4, 0.376 g (yield: 52%).

Example 7

Preparation of Pergolide (4) from 8a

LAH (0.6 g, 0.0156 mol) was slowly added to a solution of 8a (0.27 g, 0.0007 mol) in the 20 mL anhydrous THF at 0° C. under a nitrogen atmosphere. The mixture was stirred at 0° C. for 30 min and then at room temperature for 4 hours. The reaction was cooled to 0° C. and 0.6 mL of water was slowly added. The mixture was stirred at 0° C. for 10 min and 1.8 mL of 15% NaOH(aq) and 2.5 mL of water were added respectively. The mixture was stirred for 30 min. at room temperature and then filtered. Excess of the solvent was removed under reduced pressure to give a residue.

The residue was purified by a silica gel column, eluting with ethyl acetate to give 150 mg of pergolide (4), (yield: 68%).

Spectra Data of the Synthesis Compounds:

| | MS (EI) | | | | | |
|---|---|---|---|---|---|---|
| | No. of Compd. | | | | | |
| | 1 | 5a | 6a | 4 | 7a | 8a |
| M.W. | 256 | 410 | 284 | 314 | 286 | 384 |
| | FT-IR: | | | | | |
| | No. of Compd. | | | | | |
| | 1 | 5a | 6a | 4 | 7a | 8a |
| Peak | 3418 (OH) | 1736 | 3311 (OH) | 3100 | 3144 (NH) | 1697 |
| | 3109 (NH) | (COOR) | 3.80 (NH) | (NH) | | $(CON^1)$ |
| | 1701 | | | | 1632 | |
| | $(CON^1)$ | | | | $(CON^6)$ | |

-continued 1627
(CON⁶)

| | ¹H—NMR *:CDCl₃ **: d6-DMSO | | | | | |
|---|---|---|---|---|---|---|
| | Compd. No. | | | | | |
| No. of H | 1* | 5a* | 6a** | 4* | 7a* | 8a* |
| 2 | 6.96 | 7.13 | 6.97 | 6.87 | 6.87 | 7.12 |
| 4a | 2.51 | 2.69 | 2.72 | 2.68 | 2.80 | 2.76 |
| 4b | 3.31 | 3.36 | 3.30 | 3.36 | 3.40 | 3.53 |
| 5 | 1.90 | 3.92 | 2.29 | 2.18 | 2.18 | 3.94 |
| 7a | 1.79 | 3.37 | 1.99 | 2.06 | 1.92 | 2.85 |
| 7b | 2.95 | 3.87 | 3.08 | 2.52 | 2.63 | 3.80 |
| 8 | 1.91 | 2.37 | 1.89 | 2.16 | 2.18 | 2.23 |
| 9a | 0.95 | 1.02 | 0.94 | 1.12 | 1.15 | 1.04 |
| 9b | 2.50 | 2.63 | 2.58 | 2.78 | 2.97 | 3.20 |
| 10 | 2.76 | 3.25 | 2.75 | 3.23 | 3.20 | 3.36 |
| 12 | 6.77 | 7.01 | 6.76 | 6.93 | 6.94 | 7.01 |
| 13 | 7.0I | 7.27 | 7.01 | 7.12 | 7.12 | 7.26 |
| 14 | 7.I1 | 8.08 | 7.11 | 7.15 | 7.15 | 8.06 |
| 18a | 3.31 | 3.88 | 3.31 | 2.45 | 2.43 | 2.45 |
| 18b | 3.42 | 4.16 | 3.45 | 2.50 | 2.50 | 2.57 |
| Me—N6 | 2.46 | — | — | — | 2.48 | — |
| Me—S | — | — | — | 2.14 | 2.13 | 2.12 |
| EtCO—N1 | — | 1.31, 2.88 | — | — | — | 1.30, 2.88 |
| EtCO—N6 | — | 1.13, 2.36 | — | — | — | 1.15, 2.38 |
| EtCO—O | — | 1.13, 2.36 | — | — | — | — |
| HO—C18 | 4.62 | — | 4.59 | — | — | — |
| H—N1 | 10.60 | — | 10.62 | 7.89 | 7.92 | — |
| Pr—N6 | | | 0.88, 1.45, 2.50 | 0.89, 1.53, 2.81 | — | — |

It is understood that the examples and embodiments described herein are for illustrative purposes only and that various modifications or changes in light thereof will be suggested to one skilled in the art and are to be included in the spirit of this application and scope of the appended claims.

What is claimed is:

1. A process for preparing pergolide, comprising the following steps:
    (a) reacting 9,10-dihydrolysergol with an acid anhydride at an elevated temperature in the presence of a catalyst to form the corresponding triacylated product;
    (b) reducing the triacylated product with a reducing agent in a solvent to form the corresponding primary amino alcohol; and
    (c) reacting the amino alcohol with dimethyl disulfide and trialkyl phosphine, aryl phosphine or the polymeric derivatives of phosphine analogs thereof, in a polar solvent to form the pergolide product.

2. The process of claim 1, wherein step (a) is conducted at a temperature in the range of 100° C. to 200° C.

3. The process of claim 1, wherein the acid anhydride of step (a) is selected from the group consisting of acetic anhydride, propionic anhydride, butyric anhydride, and pentanoic anhydride.

4. The process of claim 1, wherein the catalyst of step (a) is selected from sodium iodide or dimethylaminopyridine.

5. The process of claim 1, wherein step (a) is conducted in a highly polar solvent.

6. The process of claim 1, wherein the reducing agent of step (b) is lithium aluminum hydride.

7. The process of claim 1, wherein the solvent for step (b) is tetrahydrofuran.

8. The process of claim 1, wherein in step (c) the trialkyl phosphine has the formula of R₃P, wherein R is (CH₂)ₙ and n is 1–6, and the aryl phosphine has the formula of Ar₃P, wherein Ar is phenyl or substituted phenyl.

9. The process of claim 1, wherein the polar solvent of step (c) is selected from dimethyl formamide or dimethylsulfoxide.

10. The process of claim 1, wherein the triacylated product from step (a) is D-1,6-dipropionyl-8β-(propionyloxymethyl)ergoline and the primary amino alcohol from step (b) is D-6n-propyl-8β-hydroxymethylergoline.

11. The process of claim 1, wherein step (a) is conducted at a temperature in the range of 100° C. to 200° C.; the acid anhydride is selected from the group consisting of acetic anhydride, propionic anhydride, butyric anhydride, and pentanoic anhydride; the catalyst of step (a) is sodium iodide; the reducing agent of step (b) is lithium aluminum hydride; the solvent for step (b) is tetrahydrofuran; the trialkyl phosphine has the formula of R₃P, wherein R is (CH₂)ₙ and n is 1–6, and the aryl phosphine has the formula of Ar₃P, wherein Ar is phenyl or substituted phenyl; and the polar solvent of step (c) is dimethyl formamide.

12. A process for preparing pergolide, comprising the following steps:
    (a) reacting 9,10-dihydrolysergol with dimethyl disulfide and trialkyl phosphine, aryl phosphine or the polymeric derivatives of phosphine analogs thereof, in a polar solvent to form the corresponding methyl sulfide;
    (b) reacting the methyl sulfide with an acid anhydride at an elevated temperature in the presence of a catalyst to form the corresponding diacylated amide intermediate; and
    (c) reducing the diacylated amide with a reducing agent in a solvent to obtain the pergolide product.

13. The process of claim 12, wherein in step (a) the trialkyl phosphine has the formula of R₃P, wherein R is (CH₂)ₙ and n is 1–6, and the aryl phosphine has the formula of Ar₃P, wherein Ar is phenyl or substituted phenyl.

14. The process of claim 12, wherein the polar solvent of step (a) is selected from dimethyl formamide or dimethylsulfoxide.

15. The process of claim 12, wherein step (b) is conducted at a temperature in the range of 100° C. to 200° C.

16. The process of claim 12, wherein the acid anhydride of step (b) is selected from the group consisting of acetic anhydride, propionic anhydride, butyric anhydride, and pentanoic anhydride.

17. The process of claim 12, wherein the catalyst of step (b) is selected from sodium iodide or dimethylaminopyridine.

18. The process of claim 12, wherein step (b) is conducted in a highly polar solvent.

19. The process of claim 12, wherein the reducing agent of step (c) is lithium aluminum hydride.

20. The process of claim 12, wherein the solvent for step (c) is tetrahydrofuran.

21. The process of claim 12, wherein the trialkyl phosphine has the formula of R₃P, wherein R is (CH₂)ₙ and n is 1–6, and the aryl phosphine has the formula of Ar₃P, wherein Ar is phenyl or substituted phenyl; the polar solvent of step (a) is dimethyl formamide; step (b) is conducted at a temperature in the range of 100° C. to 200° C.; the acid anhydride is selected from the group consisting of acetic anhydride, propionic anhydride, butyric anhydride, and pentanoic anhydride; the catalyst of step (b) is sodium iodide; the reducing agent of step (c) is lithium aluminum hydride; and the solvent for step (c) is tetrahydrofuran.

* * * * *

UNITED STATES PATENT AND TRADEMARK OFFICE
CERTIFICATE OF CORRECTION

PATENT NO. : 6,388,079 B1
DATED : May 14, 2002
INVENTOR(S) : Wu et al.

It is certified that error appears in the above-identified patent and that said Letters Patent is hereby corrected as shown below:

Title page,
Item [57], ABSTRACT, replace

Replace "This invention relates to a process for preparing pergolide, which comprises the steps of reacting 9, 10-dihydrolysergol with an anhydride at an elevated temperature in the presence of a catalyst to form a triacylated product intermediate; reducing the triacylated product intermediate with a reducing agent in a solvent to form a primary amino alcohol intermediate; and reacting the amino alcohol intermediate with dimethyl disulfide and trialkyl phosphine, aryl phosphine or the polymeric derivatives of phosphine analogs thereof in a polar solvent to obtain pergolide; or the steps of reacting 9, 10-dihydrolysergol with dimethyl disulfide and trialkyl phosphine, aryl phosphine or the polymeric derivatives of phosphine analogs thereof in a polar solvent to form a methylsulfide intermediate; reacting the methylsulfide intermediate with an acid anhydrife at an elevated temperature in the presence of a catalyst to form a diacylated amide intermediate; and reducing the deacylated amide intermediate with a reducing agent in a solvent to obtain pergolide. "

With --A process for preparing pergolide comprises the steps of reacting 9, 10-dihydrolysergol with an anhydride at an elevated temperature in the presence of a catalyst to form a triacylated product intermediate; reducing the triacylated product intermediate with a reducing agent in a solvent to form a primary amino alcohol intermediate; and reacting the amino alcohol intermediate with dimethyl disulfide and trialkyl phosphine, aryl phosphine or the polymeric derivatives of phosphine analogs thereof in a polar solvent to obtain pergolide; or the steps of reacting 9, 10-dihydrolysergol with dimethyl disulfide and trialkyl phosphine, aryl phosphine or the polymeric derivatives of phosphine analogs thereof in a polar solvent to form a methylsulfide intermediate; reacting the methylsulfide intermediate with an acid anhydrife at an elevated temperature in the presence of a catalyst to form a diacylated amide intermediate; and reducing the deacylated amide intermediate with a reducing agent in a solvent to obtain pergolide. --

UNITED STATES PATENT AND TRADEMARK OFFICE
CERTIFICATE OF CORRECTION

PATENT NO. : 6,388,079 B1
DATED : May 14, 2002
INVENTOR(S) : Wu et al.

It is certified that error appears in the above-identified patent and that said Letters Patent is hereby corrected as shown below:

Column 12,
Line 60,

Replace "

FT-IR:

| No. of Comp. | 1 | 5a | 6a | 4 | 7a | 8a |
|---|---|---|---|---|---|---|
| Peak | 3418 (OH) 3109 (NH) 1701 (CON$^1$) 1627 (CON$^6$) | 1736 (COOR) | 3311 (OH) 3.80 (NH) | 3100 (NH) | 3144 (NH) 1632 (CON$^6$) | 1697 (CON$^1$) |

"
With --

FT-IR:

| No. of Comp. | 1 | 5a | 6a | 4 | 7a | 8a |
|---|---|---|---|---|---|---|
| Peak | 3418 (OH) 3109 (NH) | 1736 (COOR) 1701 (CON$^1$) 1627 (CON$^6$) | 3311 (OH) 3.80 (NH) | 3100 (NH) | 3144 (NH) | 1697 (CON$^1$) 1632 (CON$^6$) |

--

Signed and Sealed this

Fifth Day of August, 2003

JAMES E. ROGAN
*Director of the United States Patent and Trademark Office*